(12) United States Patent
Yu et al.

(10) Patent No.: US 11,876,177 B2
(45) Date of Patent: Jan. 16, 2024

(54) NON-AQUEOUS ELECTROLYTE SOLUTION FOR LITHIUM SECONDARY BATTERY AND LITHIUM SECONDARY BATTERY INCLUDING THE SAME

(71) Applicant: LG Chem, Ltd., Seoul (KR)

(72) Inventors: Sung Hoon Yu, Daejeon (KR); Chul Haeng Lee, Daejeon (KR); Hyun Seung Kim, Daejeon (KR)

(73) Assignee: LG Energy Solution, Ltd.

( * ) Notice: Subject to any disclaimer, the term of this patent is extended or adjusted under 35 U.S.C. 154(b) by 299 days.

(21) Appl. No.: 16/606,972

(22) PCT Filed: Aug. 24, 2018

(86) PCT No.: PCT/KR2018/009790
§ 371 (c)(1),
(2) Date: Oct. 21, 2019

(87) PCT Pub. No.: WO2019/039903
PCT Pub. Date: Feb. 28, 2019

(65) Prior Publication Data
US 2020/0335822 A1    Oct. 22, 2020

(30) Foreign Application Priority Data

Aug. 24, 2017 (KR) ................ 10-2017-0107484
Aug. 23, 2018 (KR) ................ 10-2018-0098366

(51) Int. Cl.
*H01M 10/0567* (2010.01)
*C07C 69/96* (2006.01)
(Continued)

(52) U.S. Cl.
CPC ......... *H01M 10/0567* (2013.01); *C07C 69/96* (2013.01); *C07C 305/14* (2013.01);
(Continued)

(58) Field of Classification Search
None
See application file for complete search history.

(56) References Cited

U.S. PATENT DOCUMENTS

2006/0177742 A1* 8/2006 Abe ................ H01M 10/0568
429/330
2011/0223489 A1* 9/2011 Iwanaga ............ H01M 10/052
429/340
(Continued)

FOREIGN PATENT DOCUMENTS

CN    105609877 A    5/2016
JP    2000195545 A * 7/2000
(Continued)

OTHER PUBLICATIONS

English language machine translation of Ihara et al. (JP 2011-238373 A). (Year: 2023).*
(Continued)

*Primary Examiner* — Eli S Mekhlin
(74) *Attorney, Agent, or Firm* — Lerner David LLP (57) ABSTRACT

A non-aqueous electrolyte solution for a lithium secondary battery and a lithium secondary battery including the same are disclosed herein. In some embodiments, a non-aqueous electrolyte solution for a lithium secondary battery, includes an additive having metal ion adsorbability and capable of forming a stable ion conductive film on the surface of an electrode. In some embodiments, a lithium secondary battery including the same has an improved an abnormal voltage drop phenomenon.

12 Claims, 1 Drawing Sheet

(51) Int. Cl.
- *C07C 305/14* (2006.01)
- *C07C 305/18* (2006.01)
- *C07C 309/67* (2006.01)
- *H01M 10/0525* (2010.01)
- *H01M 10/0568* (2010.01)

(52) U.S. Cl.
CPC .......... *C07C 305/18* (2013.01); *C07C 309/67* (2013.01); *H01M 10/0525* (2013.01); *H01M 10/0568* (2013.01); *H01M 2300/0025* (2013.01)

(56) References Cited

U.S. PATENT DOCUMENTS

| | | |
|---|---|---|
| 2011/0223490 A1 | 9/2011 | Andou et al. |
| 2012/0258357 A1 | 10/2012 | Kim |
| 2015/0191423 A1 | 7/2015 | Bomkamp et al. |
| 2015/0333370 A1 | 11/2015 | Abe et al. |
| 2016/0028115 A1* | 1/2016 | Kim .................. H01M 10/0568 429/200 |
| 2016/0254572 A1* | 9/2016 | Yu ........................ H01M 4/661 429/126 |
| 2017/0194664 A1 | 7/2017 | Abe et al. |
| 2018/0301758 A1 | 10/2018 | Abe et al. |
| 2018/0358655 A1 | 12/2018 | Kono et al. |
| 2020/0058959 A1* | 2/2020 | Morino ............. H01M 10/0568 |

FOREIGN PATENT DOCUMENTS

| | | | |
|---|---|---|---|
| JP | 2001256995 A | | 9/2001 |
| JP | 2007066864 A | | 3/2007 |
| JP | 200993839 A | | 4/2009 |
| JP | 2009093839 A | * | 4/2009 |
| JP | 2011238373 A | * | 11/2011 |
| JP | 2015530972 A | | 10/2015 |
| KR | 20110102831 A | | 9/2011 |
| KR | 20120115839 A | | 10/2012 |
| KR | 20150046050 A | | 4/2015 |
| KR | 20160036809 A | | 4/2016 |
| WO | 2015182690 A1 | | 12/2015 |
| WO | 2016158986 A1 | | 10/2016 |
| WO | 2017061464 A1 | | 4/2017 |

OTHER PUBLICATIONS

English language machine translation of Abe et al. (JP 2009-093839 A). (Year: 2023).*

English language machine translation of JP 2000195545 A, Abstract 1. (Year: 2023).*

English language machine translation of JP 2000195545 A, Abstract 2. (Year: 2023).*

Ciosek et al., "The Influence of PMS-Additive on the Electrode/Electrolyte Interfaces in LiFePO4/Graphite Li-Ion Batteries", The Journal of Physical Chemistry, vol. 117, Oct. 2013, pp. 23476-23486.

International Search Report from Application No. PCT/KR2018/009790 dated Mar. 22, 2019, pp. 1-2.

* cited by examiner

NON-AQUEOUS ELECTROLYTE SOLUTION FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2018/009790, filed on Aug. 24, 2018, which claims priority from Korean Patent Application Nos. 10-2017-0107484, filed on Aug. 24, 2017, and 10-2018-0098366, filed on Aug. 23, 2018, the disclosures of which are incorporated by reference herein.

TECHNICAL FIELD

The present invention relates to a non-aqueous electrolyte solution for a lithium secondary battery and a lithium secondary battery including the same.

BACKGROUND ART

In line with miniaturization, lightweight, thin profile, and portable trends in electronic devices according to the development of information and telecommunications industry, the need for high energy density batteries used as power sources of such electronic devices has increased.

Lithium secondary batteries, specifically, lithium ion batteries (LIB), as batteries that may best meet the need, have been adopted as power sources of many portable devices due to high energy density and ease of design.

Recently, a lithium secondary battery, which may maintain excellent performance not only at room temperature but also in a more severe outside environment such as a high-temperature or low-temperature environment, is required as the range of the lithium secondary batteries used has expanded from conventional small electronic devices to large electronic devices, cars, or smart grids.

A lithium secondary battery currently used is composed of a carbon-based negative electrode capable of intercalating and deintercalating lithium ions, a lithium-containing transition metal oxide-based positive electrode, and a non-aqueous electrolyte solution in which an appropriate amount of a lithium salt is dissolved in a mixed carbonate-based organic solvent, wherein charge and discharge may be possible, because lithium ions, which are discharged from the positive electrode by charging, transfer energy while a phenomenon is repeated in which the lithium ions are intercalated into the negative electrode, for example, carbon particles, and deintercalated during discharging.

Metal ions are dissolved from the surface of the positive electrode while a positive electrode active material is structurally collapsed as charge and discharge of the lithium secondary battery proceed. The dissolved metal ions are electrodeposited on the negative electrode to degrade the negative electrode. The degradation phenomenon is further accelerated when the potential of the positive electrode is increased or the battery is exposed to high temperature.

In order to address this limitation, a method of adding compounds capable of forming a protective layer in the non-aqueous electrolyte solution, that is, a solid electrolyte interface (SEI) on the surface of the negative electrode has been suggested. However, another limitation may occur in which overall performance of the secondary battery is degraded as other side effects are caused by these electrolyte solution additives.

Thus, there is a continuous need to develop a non-aqueous electrolyte solution containing an additive which may improve performance and stability of the battery while minimizing the side effects.

PRIOR ART DOCUMENT

Japanese Patent Application Laid-open Publication No. 2007-066864

DISCLOSURE OF THE INVENTION

Technical Problem

An aspect of the present invention provides a non-aqueous electrolyte solution for a lithium secondary battery which includes an additive having metal ion adsorbability and capable of forming a stable ion conductive film on the surface of an electrode.

Another aspect of the present invention provides a lithium secondary battery in which an abnormal voltage drop phenomenon during high-temperature storage is improved by including the non-aqueous electrolyte solution for a lithium secondary battery.

Technical Solution

According to an aspect of the present invention, there is provided a non-aqueous electrolyte solution for a lithium secondary battery including:

a first lithium salt which is lithium bis(fluorosulfonyl)imide (LiFSI);

a second lithium salt excluding the lithium bis(fluorosulfonyl)imide;

an organic solvent; and a compound represented by Formula 1 below.

(Formula 1)

In Formula 1, $R_1$ to $R_3$ are each independently hydrogen or an alkyl group having 1 to 6 carbon atoms, and A is wherein, $R_4$ to $R_6$ are each independently hydrogen, an alkyl group having 1 to 6 carbon atoms which is unsubstituted or substituted with at least one fluorine atom, a substituted or unsubstituted aryl group having 6 to 8 carbon atoms, an aryl group having 6 to 8 carbon atoms which is substituted with at least one fluorine atom, or an alkynyl group having 2 to 6 carbon atoms.

The first lithium salt may be included in a concentration of 0.01 M to 3 M in the non-aqueous electrolyte solution.

Also, a molar ratio of the second lithium salt to the first lithium salt may be in a range of 1:0.01 to 1:100, particularly 1:0.01 to 1:20, and more particularly 1:0.2 to 1:10.

Furthermore, in the compound represented by Formula 1, the substituted aryl group having 6 to 8 carbon atoms may be a phenyl group substituted with an alkyl group having 1 to 3 carbon atoms, and the aryl group having 6 to 8 carbon atoms which is substituted with at least one fluorine atom may be a phenyl group substituted with at least one fluorine atom.

Specifically, the compound represented by Formula 1 may be at least one selected from the group consisting of compounds represented by Formulae 1a to 1o.

Specifically, the compound represented by Formula 1 may be at least one selected from the group consisting of compounds represented by Formulae 1a to 1l.

The compound represented by Formula 1 may be included in an amount of 0.01 wt % to 10 wt %, particularly 0.1 wt % to 7 wt %, and more particularly 0.5 wt % to 7 wt % based on a total weight of the non-aqueous electrolyte solution for a secondary battery.

According to another aspect of the present invention, there is provided a lithium secondary battery including the non-aqueous electrolyte solution for a lithium secondary battery of the present invention.

Advantageous Effects

According to the present invention, a non-aqueous electrolyte solution for a lithium secondary battery, which may suppress a side effect in a battery caused by metallic foreign matter, may be prepared by including both a first lithium salt promoting the dissolution of the metallic foreign matter from a positive electrode and a compound containing a propargyl group having metal ion adsorbability. Also, a lithium secondary battery may be prepared in which an abnormal voltage drop phenomenon during high-temperature storage is improved by including the non-aqueous electrolyte solution for a lithium secondary battery.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

In general, when overcharging of a secondary battery occurs, a structure of a positive electrode active material becomes in an unstable state while an excessive amount of lithium ions is discharged from a positive electrode. As a result, oxygen is released from the positive electrode active material, and the released oxygen causes a decomposition reaction of an electrolyte solution. The dissolution of metallic foreign matter, such as cobalt (Co), manganese (Mn), and nickel (Ni), from the positive electrode active material is increased by structural collapse of the positive electrode active material and a side reaction with the electrolyte solution, and the dissolved metallic foreign matter moves to a negative electrode and precipitates as dendrites on a surface of the negative electrode to cause a micro-short circuit between the positive electrode and the negative electrode. Overall performance of the battery is degraded while an abnormal voltage drop phenomenon, in which a voltage of the battery is reduced, occurs due to the short circuit. In this case, the low-voltage phenomenon may also be caused by metallic foreign matter which is included in raw materials of the lithium battery or incorporated in a preparation process.

In the present invention, in order to improve these limitations, provided is a non-aqueous electrolyte solution which includes a first lithium salt promoting the dissolution of the metallic foreign matter and a compound, which performs a passivation function to prevent the dissolved metallic foreign matter from growing on the surface of the negative electrode as dendrites by adsorbing metal ions, as an additive.

Also, in the present invention, provided is a lithium secondary battery in which the low voltage failure rate is improved even after high-temperature storage by including the non-aqueous electrolyte solution.

Non-Aqueous Electrolyte Solution

Specifically, in an embodiment of the present invention, provided is a non-aqueous electrolyte solution for a lithium secondary battery including:

a first lithium salt which is lithium bis(fluorosulfonyl)imide (LiFSI);

a second lithium salt excluding the lithium bis(fluorosulfonyl)imide (LiFSI);

an organic solvent, and a compound represented by Formula 1 below.

(Formula 1)

In Formula 1, $R_1$ to $R_3$ are each independently hydrogen or an alkyl group having 1 to 6 carbon atoms, and A is wherein, $R_4$ to $R_6$ are each independently hydrogen, an alkyl group having 1 to 6 carbon atoms which is unsubstituted or substituted with at least one fluorine atom, a substituted or unsubstituted aryl group having 6 to 8 carbon atoms, an aryl group having 6 to 8 carbon atoms which is substituted with at least one fluorine atom, or an alkynyl group having 2 to 6 carbon atoms.

Specifically, the substituted aryl group having 6 to 8 carbon atoms is a phenyl group substituted with an alkyl group having 1 to 3 carbon atoms, and the aryl group having 6 to 8 carbon atoms which is substituted with at least one fluorine atom is a phenyl group substituted with at least one fluorine atom.

(1) First Lithium Salt

First, in the non-aqueous electrolyte solution for a lithium secondary battery according to the embodiment of the present invention, lithium bis(fluorosulfonyl)imide, as the first lithium salt, is a component capable of promoting the dissolution of metallic foreign matter, wherein it may be included in a concentration of 0.01 M to 3 M, for example, 0.2 M to 2 M in the non-aqueous electrolyte solution.

When the concentration of the lithium bis(fluorosulfonyl)imide satisfies the above range, high-temperature cycle characteristics may be improved by preventing a side reaction in the electrolyte solution during charge and discharge of the secondary battery, and, particularly, in a case in which the lithium bis(fluorosulfonyl)imide is included in a concentration of 0.01 M or more, for example, 0.2 M or more, low-voltage failure after high-temperature storage may be further improved by promoting the dissolution of the metallic foreign matter.

In a lithium secondary battery, structural collapse of $LiCoO_2$, $LiMn_2O_4$, or $LiNiO_2$, as a positive electrode active material, or a chemical dissolution reaction by the electrolyte solution occurs by repeated charge and discharge cycles so that metallic foreign matter, such as cobalt (Co), manganese (Mn), nickel (Ni), iron (Fe), and aluminum (Al), is dissolved from the positive electrode active material. The dissolved metallic foreign matter not only degrades performance of a positive electrode, but also causes a phenomenon in which the dissolved metallic foreign matter is electrodeposited and precipitated on the surface of a negative electrode. Since the metallic foreign matter electrodeposited on the negative electrode reduces the mobility of lithium ions while exhibiting a high reactivity with respect to the electrolyte solution, an irreversible reaction is increased and, as a result, capacity and charge and discharge efficiency of the battery are reduced.

Typically, a method has been proposed in which the dissolution of the metallic foreign matter present in the battery is suppressed by including an additive in the electrolyte solution. However, it is not known how long the suppression reaction by the additive will last, and furthermore, the suppression effect is not only reduced over time, but the low-voltage phenomenon may also occur when the dissolution of the metallic foreign matter can no longer be suppressed.

Therefore, the present invention aims at removing a potential metallic foreign matter dissolution factor by increasing a dissolution effect so that the metallic foreign matter, which is included in raw materials of the lithium battery or incorporated in the preparation process, may be dissolved from the positive electrode at the beginning of charge and discharge by including the first lithium salt capable of promoting the dissolution of the metallic foreign matter as a non-aqueous electrolyte solution component.

For example, metallic foreign matter incorporated in the battery preparation process during charge and discharge, for example, $Cr^{2+}$, one of stainless steel components induced by stainless steel manufacturing equipment, bonds with a $F^{31}$ ion generated from a lithium salt ($LiPF_6$) included in the electrolyte solution to form a F-based passive film (e.g., $CrF_3$) on a surface of the positive electrode. Since the film is gradually destroyed over time after high-temperature storage, continuous metal ion dissolution occurs.

Figure 1:
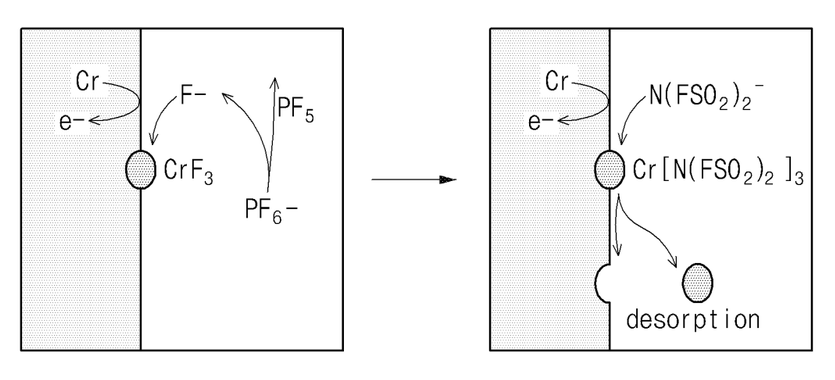
FIG. 1 is a view for explaining a reaction mechanism in which metal dissolution is increased by a first lithium salt in the present invention.

In the present invention, since a formation reaction of the F-based passive film is suppressed by a reaction of an $N(FSO_2)_2^-$ anion of the first lithium salt with $Cr^{2+}$ by including the lithium bis(fluorosulfonyl)imide as the first lithium salt (see FIG. 1) and, as a result, the potential metallic foreign matter dissolution factor is removed, the low-voltage failure after high-temperature storage or after shipment may be improved. Furthermore, since a low voltage is generated in the preparation process to facilitate the detection of defective cells when an initial dissolution rate of the metallic foreign matter is significantly increased, shipment of the low-voltage defective cells may not only be prevented, but the low voltage generation may also be prevented in advance because an amount of the metallic foreign matter dissolved is insignificant even if the metallic foreign matter is dissolved after the shipment.

(2) Second Lithium Salt

Any lithium salt typically used in an electrolyte solution for a lithium secondary battery and different from the first lithium salt may be used as the second lithium salt without limitation, and, for example, the second lithium salt may include $Li^+$ as a cation, and may include at least one selected from the group consisting of $F^-$, $Cl^-$, $Br^-$, $I^-$, $NO_3^-$, $N(CN)_2^-$, $BF_4^-$, $ClO_4^-$, $AlO_4^-$, $ACl_4^-$, $PF_6^-$, $SbF_6^-$, $AsF_6^-$, $BF_2C_2O_4^-$, $BC_4O_8^-$, $PO_2F_2^-$, $PF_4C_2O_4^-$, $PF_2C_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $CF_3CF_2(CF_3)_2CO^-$, $(CF_3SO_2)_2CH^-$, $(SF_5)_3C^-$, $(CF_3S_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion.

The second lithium salt may be appropriately changed in a normally usable range, but may be included in a concentration of 1.5 M or less, for example, 0.1 M to 1.5 M in the electrolyte solution in order to obtain an optimum anti-corrosion film-forming effect on the surface of the electrode. If the concentration of the electrolyte salt is greater than 1.5 M, the film-forming effect may be reduced.

In the non-aqueous electrolyte solution for a lithium secondary battery according to the embodiment of the present invention, a molar ratio of the second lithium salt to the lithium bis(fluorosulfonyl)imide, as the first lithium salt, may be appropriately varied within a range of 1:0.01 to 1:100, but the molar ratio may be in a range of 1:0.01 to 1:20, particularly 1:0.2 to 1:10, and more particularly 1:0.2 to 1:2.

When the relative molar ratio of the first lithium salt with respect to 1 mole of the second lithium salt satisfies the above range condition, the dissolution rate of the metallic foreign matter from the positive electrode may be controlled, and, furthermore, a swelling phenomenon may be prevented by suppressing the excessive occurrence of side reactions in the electrolyte solution during charge and discharge of the secondary battery. Also, since the exfoliation of a negative electrode surface layer (e.g., carbon surface layer) and the decomposition of the electrolyte solution may be prevented by suppressing an irreversible reaction during the formation of a solid electrolyte interface (SEI) in the lithium ion battery or during the intercalation of lithium ions solvated by a carbonate-based solvent into the negative electrode, safety and output characteristics of the secondary battery may be improved.

That is, in a case in which the molar ratio of the first lithium salt with respect to 1 mole of the second lithium salt is less than 0.01, for example, the first lithium salt is included in an amount of less than 0.01 mole, since the decomposition of the first lithium salt is small at a high temperature but the second lithium salt (e.g., $LiPF_6$) is relatively well decomposed, a side reaction, such as an increase in resistance, may occur, and thus, high-temperature storage performance may be degraded.

(3) Organic Solvent

A type of the organic solvent is not limited as long as the organic solvent may minimize decomposition due to an oxidation reaction during charge and discharge of the secondary battery and may exhibit desired characteristics with the additive. For example, an ether-based solvent, an ester-based solvent, or an amide-based solvent may be used alone or as a mixture of two or more thereof.

As the ether-based solvent among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a cyclic carbonate compound, a linear carbonate compound, an alkyl ether-based compound, an alkyl acetate-based compound, and an alkyl propionate-based compound.

Among these compounds, specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

Specific examples of the alkyl ether-based compound may be at least one selected from the group consisting of dimethyl ether, diethyl ether, dipropyl ether, methyl ethyl ether, methyl propyl ether, and ethyl propyl ether.

The alkyl acetate-based compound may include at least one selected from the group consisting of methyl acetate, ethyl acetate, and propyl acetate.

The alkyl propionate-based compound may include at least one selected from the group consisting of methyl propionate, ethyl propionate, propyl propionate, and butyl propionate.

Particularly, among the ester-based solvents, since the cyclic carbonate-based compound well dissociates the lithium salt in the electrolyte due to high permittivity as a highly viscous organic solvent. Thus, an electrolyte solution having high electrical conductivity may be prepared when the above cyclic carbonate-based compound is mixed with the low viscosity, low permittivity linear carbonate-based compound, such as dimethyl carbonate and diethyl carbonate, in an appropriate ratio and used.

(4) Additive

Also, the non-aqueous electrolyte solution according to the embodiment of the present invention may include the compound represented by Formula 1 as an additive.

That is, since the compound represented by Formula 1, which is provided as a non-aqueous electrolyte solution additive in the present invention, includes both (i) a triple-bond-containing propargyl group which is known to have metal ion adsorbability and (ii) an oxygen atom in its structure, the compound represented by Formula 1 may easily adsorb on metallic foreign matter, such as Fe, Co, Mn, and Ni, dissolved from the positive electrode or metallic foreign matter, such as copper (Cu), dissolved from the negative electrode during charge and discharge, or metallic foreign matter incorporated from raw materials or in the preparation process. As a result, since the compound represented by Formula 1 may suppress the growth of the dissolved metallic foreign matter into dendrites by the electrodeposition of the dissolved metallic foreign matter on the negative electrode, the low voltage generation due to the dissolved metallic foreign matter may be prevented.

Furthermore, since the compound represented by Formula 1 containing the propargyl group may be reduced on the surface of the negative electrode to form a stable ion conductive film on the surface of the negative electrode when a predetermined voltage is reached during charge and discharge, an additional electrolyte solution decomposition reaction may be suppressed and, furthermore, the low voltage generation in the secondary battery, cycle life characteristics, and high-temperature storage performance may be improved by facilitating intercalation and deintercalation of lithium ions into and from the negative electrode even during overcharge or high-temperature storage.

In conclusion, since the non-aqueous electrolyte solution according to the embodiment of the present invention includes both the second lithium salt and the compound represented by Formula 1, a secondary battery having excellent efficiency in high-temperature safety and cycle capacity characteristics may be achieved while maintaining a stable voltage by removing metallic foreign matter even if the metallic foreign matter is present.

The compound represented by Formula 1 may be at least one selected from the group consisting of compounds represented by Formulae 1a to 1o below.

(Formula 1a)
(Formula 1b)
(Formula 1c)
(Formula 1d)
(Formula 1e)

(Formula 1f)

(Formula 1g)

(Formula 1h)

(Formula 1i)

(Formula 1j)

(Formula 1k)

(Formula 1l)

(Formula 1m)

(Formula 1n)

(Formula 1o)

Specifically, the compound represented by Formula 1 may be at least one selected from the group consisting of compounds represented by Formulae 1a to 1l.

That is, since the compounds represented by Formulae 1a to 1g contain a "—OCO$_2$R$_4$" group having a size smaller than that of a sulfonate anion contained in the compounds represented by Formulae 1m to 1o, the reactivity with a carbonate-based organic solvent, such as ethylene carbonate, is better while aggressiveness of anions is increased. Thus, the compounds represented by Formulae 1a to 1g may form a passive film having higher stability on the surface of the electrode in comparison to the compounds represented by Formulae 1m to 1o.

Furthermore, in a case in which fluoroethylene carbonate (FEC) is included as the organic solvent and, at the same time, the compounds represented by Formulae 1m to 1o are used together, a small amount of HF may be generated while the sulfonate anion decomposed from the compounds represented by Formulae 1m to 1o reacts with the FEC. Thus, stability of the SEI may be relatively reduced in comparison to a case where the compounds represented by Formulae 1a to 1g are included.

Also, with respect to the compounds represented by Formulae 1h to 1l containing a '—OSO$_2$—OR$_5$' group in which an oxygen-containing alkoxide group (—OR$_5$), as an electron-withdrawing group, is bonded to a '—OSO$_2$—' group, since reduction decomposition is easier, the compounds represented by Formulae 1h to 1l may form a film having higher stability in comparison to the compounds represented by Formulae 1m to 1o in which 'R$_6$', which is a functional group providing a delocalized negative charge not containing oxygen, is directly bonded to the 'OSO$_2$' group.

The compound represented by Formula 1 may be included in an amount of 0.01 wt % to 10 wt %, particularly 0.1 wt % to 7 wt %, and more particularly 0.5 wt % to 7 wt % based on a total amount of the non-aqueous electrolyte solution.

In a case in which the compound represented by Formula 1 is included in an amount within the above range, a secondary battery having more improved overall performance may be prepared. For example, when the amount of the additive is 0.01 wt % or more, particularly 0.1 wt % or more, and more particularly 0.5 wt % or more, a stabilization effect or dissolution suppression effect may be obtained during the formation of the SEI while suppressing an increase in resistance as much as possible, and, when the amount of the additive is 10 wt % or less, for example, 7 wt % or less, the maximum metallic foreign matter adsorption effect may be obtained within the range of increase in resistance which may be accommodated.

(5) Additional Additive

In order to further improve low-temperature high-rate discharge characteristics, high-temperature stability, overcharge protection, and an effect of improving swelling during high-temperature storage, the non-aqueous electrolyte solution for a lithium secondary battery of the present invention may further include an additional additive capable of forming a more stable ion conductive film on the surface of the electrode, if necessary.

Specifically, as a representative example, the additional additive may include at least one selected from the group consisting of a sultone-based compound, a halogen-substituted carbonate-based compound, a nitrile-based compound, a cyclic sulfite-based compound, and a cyclic carbonate-based compound.

The sultone-based compound may include at least one compound selected from the group consisting of 1,3-propane sultone (PS), 1,4-butane sultone, ethene sultone, 1,3-propene sultone (PRS), 1,4-butene sultone, and 1-methyl-1,3-propene sultone. The sultone-based compound may be included in an amount of 0.3 wt % to 5 wt %, for example, 1 wt % to 5 wt % based on a total weight of the non-aqueous electrolyte solution. In a case in which the amount of the sultone-based compound in the non-aqueous electrolyte solution is greater than 5 wt %, since a thick film is formed due to the excessive amount of the additive, output degradation and an increase in resistance may occur.

Also, the halogen-substituted carbonate-based compound may include fluoroethylene carbonate (FEC) and may be included in an amount of 5 wt % or less based on the total weight of the non-aqueous electrolyte solution. In a case in which the amount of the halogen-substituted carbonate-based compound is greater than 5 wt %, cell swelling performance may deteriorate.

Furthermore, the nitrile-based compound may include at least one compound selected from the group consisting of succinonitrile (NA), adiponitrile (Adn), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The nitrile-based compound may be included in an amount of 5 wt % to 8 wt %, for example, 6 wt % to 8 wt % based on the total weight of the non-aqueous electrolyte solution. In a case in which the total amount of the nitrile-based compound in the non-aqueous electrolyte solution is greater than 8 wt %, since the resistance is increased due to an increase in the film formed on the surface of the electrode, battery performance may deteriorate.

Also, the cyclic sulfite-based compound may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, and may be included in an amount of 5 wt % or less based on the total weight of the non-aqueous electrolyte solution. In a case in which the amount of the cyclic sulfite-based compound is greater than 5 wt %, since a thick film is formed due to the excessive amount of the additive, the output degradation and the increase in resistance may occur.

Furthermore, the cyclic carbonate-based compound may include vinylene carbonate (VC) or vinyl ethylene carbonate, and may be included in an amount of 3 wt % or less based on the total weight of the non-aqueous electrolyte solution. In a case in which the amount of the cyclic carbonate-based compound in the non-aqueous electrolyte solution is greater than 3 wt %, cell swelling inhibition performance may deteriorate.

Secondary Battery

Also, in an embodiment of the present invention, provided is a lithium secondary battery including the electrolyte solution of the present invention.

The lithium secondary battery of the present invention may be prepared by injecting the non-aqueous electrolyte solution of the present invention into an electrode assembly composed of a positive electrode, a negative electrode, and a separator disposed between the positive electrode and the negative electrode.

In this case, any positive electrode, negative electrode, and separator, which have typically been used in the preparation of a lithium secondary battery, may be used as the positive electrode, negative electrode, and separator which constitute the electrode assembly.

First, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), etc.), or lithium-nickel-cobalt-transition metal (M) oxide (e.g., $Li(Ni_{p2}Co_{q2}Mn_{r3}M_{s2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$), etc.), and any one thereof or two or more compounds thereof may be included.

Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{1/3}Mn_{1/3}Co_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.).

The positive electrode active material may be included in an amount of 80 wt % to 99 wt % based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

The conductive agent is commonly added in an amount of 1 wt % to 30 wt % based on the total weight of the solid content in the positive electrode slurry.

Any conductive agent may be used without particular limitation so long as it has suitable conductivity without causing adverse chemical changes in the battery, and, for example, a conductive material such as: graphite; a carbon-based material such as carbon black, acetylene black, Ketjen black, channel black, furnace black, lamp black, and thermal black; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives may be used. Specific examples of a commercial conductive agent may be acetylene black-based products (Chevron Chemical Company, Denka black (Denka Singapore Private Limited), or Gulf Oil Company), Ketjen black, ethylene carbonate (EC)-based products (Armak Company), Vulcan XC-72 (Cabot Company), and Super P (Timcal Graphite & Carbon).

The solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 50 wt % to 95 wt %, for example, 70 wt % to 90 wt %.

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

Furthermore, the negative electrode active material may include a single material selected from the group consisting of a lithium-containing titanium composite oxide (LTO); a carbon-based material such as non-graphitizable carbon and graphite-based carbon; a complex metal oxide such as $Li_xFe_2O_3 (0 \leq x \leq 1)$, $Li_xWO_2$ ($0 \leq x \leq 1$), and $Sn_xMe_{1-x}Me'_yO_z$ (Me: manganese (Mn), iron (Fe), lead (Pb), or germanium (Ge); Me': aluminum (Al), boron (B), phosphorus (P), silicon (Si), Groups I, II and III elements of the periodic table, or halogen; $0<x \leq 1$; $1 \leq y \leq 3$; $1 \leq z \leq 8$); a lithium metal; a lithium alloy; a silicon-based alloy; a tin-based alloy; a metal oxide such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, and $Bi_2O_5$; and a conductive polymer, such as polyacetylene, or a mixture of two or more thereof.

The negative electrode active material may be included in an amount of 80 wt % to 99 wt % based on a total weight of solid content in the negative electrode slurry.

The binder is a component that assists in the binding between the conductive agent, the active material, and the current collector, wherein the binder is commonly added in an amount of 1 wt % to 30 wt % based on the total weight of the solid content in the negative electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode slurry. Any conductive agent may be used without particular limitation so long as it has conductivity without causing adverse chemical changes in the battery, and, for example, a conductive material, such as: graphite such as natural graphite or artificial graphite; carbon black such as acetylene black, Ketjen black, channel black, furnace black, lamp black, and thermal black; conductive fibers such as carbon fibers and metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as NMP and alcohol, and may be used in an amount such that desirable viscosity is obtained when the negative electrode active material as well as selectively the binder and the conductive agent are included. For example, the solvent may be included in an amount such that a concentration of the solid content in the slurry including the negative electrode active material as well as selectively the binder and the conductive agent is in a range of 50 wt % to 95 wt %, for example, 70 wt % to 90 wt %.

Also, the separator plays a role in blocking an internal short circuit between both electrodes and impregnating the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

After ethylene carbonate (EC) and ethyl methyl carbonate (EMC) were mixed in a ratio of 30:70 (vol %) and 1 M LiFSI, as a first lithium salt, and 1 M $LiPF_6$, as a second lithium salt, were added to prepare a mixed solution, 0.5 g of the compound of Formula 1a was added to 99.5 g of the mixed solution prepared to prepare a non-aqueous electrolyte solution of the present invention.

(Positive Electrode Preparation)

40 parts by weight of a solid, in which lithium cobalt composite oxide ($LiCoO_2$) as positive electrode active material particles, carbon black as a conductive agent, and polyvinylidene fluoride (PVDF), as a binder, were mixed in a ratio of 90:5:5 (wt %), was added to 100 parts by weight of N-methyl-2-pyrrolidone (NMP) to prepare a positive electrode active material slurry. A 100 μm thick positive electrode collector (Al thin film) was coated with the positive electrode active material slurry, dried, and roll-pressed to prepare a positive electrode.

(Negative Electrode Preparation)

100 parts by weight of a solid, in which natural graphite, as a negative electrode active material, PVDF as a binder, and carbon black, as a conductive agent, were mixed in a ratio of 95:2:3 (wt %), was added to 100 parts by weight of NMP to prepare a negative electrode active material slurry. A 90 μm thick negative electrode collector (Cu thin film) was coated with the negative electrode active material slurry, dried, and roll-pressed to prepare a negative electrode.

(Secondary Battery Preparation)

After an electrode assembly was prepared by stacking a polyethylene porous film, as a separator, with the positive electrode and negative electrode prepared by the above-described methods, the electrode assembly was put in a battery case, the non-aqueous electrolyte solution was injected thereinto, and the battery case was sealed to prepare a lithium secondary battery (battery capacity 5.5 mAh). In this case, Fe particles, as a foreign substance for evaluating the effect of adsorbing the metallic (Fe) foreign matter, having a diameter of 280 μm to 330 μm were disposed between the positive electrode and the separator.

Examples 2

A non-aqueous electrolyte solution and a secondary battery including the same were prepared in the same manner as in Example 1 except that the compound of Formula 1b, instead of the compound of Formula 1a, was added during the preparation of the non-aqueous electrolyte solution.

Example 3

A non-aqueous electrolyte solution and a secondary battery including the same were prepared in the same manner as in Example 1 except that the compound of Formula 1c, instead of the compound of Formula 1a, was added during the preparation of the non-aqueous electrolyte solution.

Example 4

A non-aqueous electrolyte solution and a secondary battery including the same were prepared in the same manner as in Example 1 except that the compound of Formula 1d, instead of the compound of Formula 1a, was added during the preparation of the non-aqueous electrolyte solution.

Example 5

A non-aqueous electrolyte solution and a secondary battery including the same were prepared in the same manner as in Example 1 except that the compound of Formula 1e, instead of the compound of Formula 1a, was added during the preparation of the non-aqueous electrolyte solution.

Example 6

A non-aqueous electrolyte solution and a secondary battery including the same were prepared in the same manner as in Example 1 except that the compound of Formula 1f, instead of the compound of Formula 1a, was added during the preparation of the non-aqueous electrolyte solution.

Example 7

A non-aqueous electrolyte solution and a secondary battery including the same were prepared in the same manner as in Example 1 except that the compound of Formula 1g, instead of the compound of Formula 1a, was added during the preparation of the non-aqueous electrolyte solution.

Example 8

A non-aqueous electrolyte solution and a secondary battery including the same were prepared in the same manner as in Example 1 except that the compound of Formula 1h, instead of the compound of Formula 1a, was added during the preparation of the non-aqueous electrolyte solution.

Example 9

A non-aqueous electrolyte solution and a secondary battery including the same were prepared in the same manner as in Example 1 except that the compound of Formula 1i, instead of the compound of Formula 1a, was added during the preparation of the non-aqueous electrolyte solution.

Example 10

A non-aqueous electrolyte solution and a secondary battery including the same were prepared in the same manner as in Example 1 except that the compound of Formula 1j, instead of the compound of Formula 1a, was added during the preparation of the non-aqueous electrolyte solution.

Example 11

A non-aqueous electrolyte solution and a secondary battery including the same were prepared in the same manner as in Example 1 except that the compound of Formula 1k, instead of the compound of Formula 1a, was added during the preparation of the non-aqueous electrolyte solution.

Example 12

A non-aqueous electrolyte solution and a secondary battery including the same were prepared in the same manner as in Example 1 except that the compound of Formula 1l, instead of the compound of Formula 1a, was added during the preparation of the non-aqueous electrolyte solution.

Example 13

A non-aqueous electrolyte solution and a secondary battery including the same were prepared in the same manner as in Example 1 except that the compound of Formula 1m, instead of the compound of Formula 1a, was added during the preparation of the non-aqueous electrolyte solution.

Example 14

A non-aqueous electrolyte solution and a secondary battery including the same were prepared in the same manner as in Example 1 except that the compound of Formula 1n, instead of the compound of Formula 1a, was added during the preparation of the non-aqueous electrolyte solution.

Example 15

A non-aqueous electrolyte solution and a secondary battery including the same were prepared in the same manner as in Example 1 except that the compound of Formula 1o, instead of the compound of Formula 1a, was added during the preparation of the non-aqueous electrolyte solution.

Example 16

A non-aqueous electrolyte solution and a secondary battery including the same were prepared in the same manner as in Example 1 except that 7 g of the compound of Formula 1a was added to 93 g of the mixed solution during the preparation of the non-aqueous electrolyte solution.

Example 17

A non-aqueous electrolyte solution and a secondary battery including the same were prepared in the same manner as in Example 1 except that ethylene carbonate (EC) and ethyl methyl carbonate (EMC) were mixed in a ratio of 30:70 (vol %) and 0.2 M LiFSI, as a first lithium salt, and 1 M $LiPF_6$, as a second lithium salt, were added to prepare a mixed solution during the preparation of the non-aqueous electrolyte solution.

Example 18

A non-aqueous electrolyte solution and a secondary battery including the same were prepared in the same manner as in Example 17 except that the compound of Formula 1b, instead of the compound of Formula 1a, was added during the preparation of the non-aqueous electrolyte solution.

Example 19

A non-aqueous electrolyte solution and a secondary battery including the same were prepared in the same manner as in Example 1 except that ethylene carbonate (EC) and ethyl methyl carbonate (EMC) were mixed in a ratio of 30:70 (vol %) and 1 M LiFSI, as a first lithium salt, and 0.1 M $LiPF_6$, as a second lithium salt, were added to prepare a mixed solution during the preparation of the non-aqueous electrolyte solution.

Example 20

A non-aqueous electrolyte solution and a secondary battery including the same were prepared in the same manner as in Example 19 except that the compound of Formula 1b, instead of the compound of Formula 1a, was added during the preparation of the non-aqueous electrolyte solution.

Example 21

A non-aqueous electrolyte solution and a secondary battery including the same were prepared in the same manner as in Example 1 except that ethylene carbonate (EC) and ethyl methyl carbonate (EMC) were mixed in a ratio of 30:70 (vol %) and 1 M LiFSI, as a first lithium salt, and 0.5

M LiPF$_6$, as a second lithium salt, were added to prepare a mixed solution during the preparation of the non-aqueous electrolyte solution.

Example 22

A non-aqueous electrolyte solution and a secondary battery including the same were prepared in the same manner as in Example 1 except that ethylene carbonate (EC) and ethyl methyl carbonate (EMC) were mixed in a ratio of 30:70 (vol %) and 0.5 M LiFSI, as a first lithium salt, and 1 M LiPF$_6$, as a second lithium salt, were added to prepare a mixed solution during the preparation of the non-aqueous electrolyte solution.

Example 23

A non-aqueous electrolyte solution and a secondary battery including the same were prepared in the same manner as in Example 1 except that 10 g of the compound of Formula 1a was added to 90 g of the mixed solution during the preparation of the non-aqueous electrolyte solution.

Example 24

A secondary battery was prepared in the same manner as in Example 1 except that, after ethylene carbonate (EC) and ethyl methyl carbonate (EMC) were mixed in a ratio of 30:70 (vol %) and 2 M LiFSI, as a first lithium salt, and 0.1 M LiPF$_6$, as a second lithium salt, were added to prepare a mixed solution, 0.1 g of the compound of Formula 1a was added to 99.9 g of the mixed solution prepared to prepare a non-aqueous electrolyte solution of the present invention during the preparation of the non-aqueous electrolyte solution.

Example 25

A non-aqueous electrolyte solution and a secondary battery including the same were prepared in the same manner as in Example 24 except that 10 g of the compound of Formula 1a was added to 90 g of the mixed solution during the preparation of the non-aqueous electrolyte solution.

Example 26

A secondary battery was prepared in the same manner as in Example 1 except that, after ethylene carbonate (EC) and ethyl methyl carbonate (EMC) were mixed in a ratio of 30:70 (vol %) and 0.01 M LiFSI, as a first lithium salt, and 1 M LiPF$_6$, as a second lithium salt, were added to prepare a mixed solution, 10 g of the compound of Formula 1a was added to 90 g of the mixed solution prepared to prepare a non-aqueous electrolyte solution of the present invention during the preparation of the non-aqueous electrolyte solution.

Example 27

A secondary battery was prepared in the same manner as in Example 1 except that 12 g of the compound of Formula 1a was added to 88 g of the mixed solution to prepare a non-aqueous electrolyte solution of the present invention during the preparation of the non-aqueous electrolyte solution.

Comparative Example 1

A non-aqueous electrolyte solution and a secondary battery were prepared in the same manner as in Example 1 except that the first lithium salt and an additive were not included during the preparation of the non-aqueous electrolyte solution.

Comparative Example 2

A non-aqueous electrolyte solution and a secondary battery were prepared in the same manner as in Example 1 except that the compound represented by Formula 1a was not included as an additive during the preparation of the non-aqueous electrolyte solution.

Comparative Example 3

A non-aqueous electrolyte solution and a secondary battery including the same were prepared in the same manner as in Example 1 except that the first lithium salt was not included during the preparation of the non-aqueous electrolyte solution.

Comparative Example 4

A non-aqueous electrolyte solution and a secondary battery were prepared in the same manner as in Example 1 except that the second lithium salt was not included during the preparation of the non-aqueous electrolyte solution.

Comparative Example 5

A non-aqueous electrolyte solution and a secondary battery were prepared in the same manner as in Example 1 except that the compound of the following Formula 2, instead of the compound of Formula 1, was included during the preparation of the non-aqueous electrolyte solution.

[Formula 2]

EXPERIMENTAL EXAMPLES

Experimental Example 1

After eight samples for each of the secondary batteries of Examples 1 to 27 and Comparative Examples 1 to 5 were prepared, each secondary battery was charged at a constant current of 0.1 C to a voltage of 4.2 V at 25° C. Thereafter, each secondary battery was charged at a constant voltage of 4.2 V and the charge was terminated when a charge current became 0.275 mA. Thereafter, after each battery was left standing for 10 minutes, each battery was discharged at a constant current of 0.5 C to a voltage of 3.0 V. The number of chargeable and dischargeable secondary batteries among the eight secondary batteries prepared in each Example and Comparative Example was checked and listed in the following Table 1.

TABLE 1

| Examples | Lithium salt concentration (M) Second lithium salt | Lithium salt concentration (M) First lithium salt | Molar ratio of second lithium salt:first lithium salt | Mixed solution (g) | Additive Formula | Additive Amount (g) | The number of chargeable and dischargeable batteries (chargeable/prepared) |
|---|---|---|---|---|---|---|---|
| Example 1 | 1 | 1 | 1:1 | 99.5 | 1a | 0.5 | 7/8 |
| Example 2 | 1 | 1 | 1:1 | 99.5 | 1b | 0.5 | 7/8 |
| Example 3 | 1 | 1 | 1:1 | 99.5 | 1c | 0.5 | 6/8 |
| Example 4 | 1 | 1 | 1:1 | 99.5 | 1d | 0.5 | 6/8 |
| Example 5 | 1 | 1 | 1:1 | 99.5 | 1e | 0.5 | 6/8 |
| Example 6 | 1 | 1 | 1:1 | 99.5 | 1f | 0.5 | 7/8 |
| Example 7 | 1 | 1 | 1:1 | 99.5 | 1g | 0.5 | 7/8 |
| Example 8 | 1 | 1 | 1:1 | 99.5 | 1h | 0.5 | 6/8 |
| Example 9 | 1 | 1 | 1:1 | 99.5 | 1i | 0.5 | 7/8 |
| Example 10 | 1 | 1 | 1:1 | 99.5 | 1j | 0.5 | 6/8 |
| Example 11 | 1 | 1 | 1:1 | 99.5 | 1k | 0.5 | 7/8 |
| Example 12 | 1 | 1 | 1:1 | 99.5 | 1l | 0.5 | 7/8 |
| Example 13 | 1 | 1 | 1:1 | 99.5 | 1m | 0.5 | 5/8 |
| Example 14 | 1 | 1 | 1:1 | 99.5 | 1n | 0.5 | 6/8 |
| Example 15 | 1 | 1 | 1:1 | 99.5 | 1o | 0.5 | 6/8 |
| Example 16 | 1 | 1 | 1:1 | 93 | 1a | 7 | 8/8 |
| Example 17 | 1 | 0.2 | 1:0.2 | 99.5 | 1a | 0.5 | 7/8 |
| Example 18 | 1 | 0.2 | 1:0.2 | 99.5 | 1b | 0.5 | 7/8 |
| Example 19 | 0.1 | 1 | 1:10 | 99.5 | 1a | 0.5 | 6/8 |
| Example 20 | 0.1 | 1 | 1:10 | 99.5 | 1b | 0.5 | 5/8 |
| Example 21 | 0.5 | 1 | 1:2 | 99.5 | 1a | 0.5 | 6/8 |
| Example 22 | 1 | 0.5 | 1:0.5 | 99.5 | 1a | 0.5 | 7/8 |
| Example 23 | 1 | 1 | 1:1 | 90 | 1a | 10 | 8/8 |
| Example 24 | 0.1 | 2 | 1:20 | 99.9 | 1a | 0.1 | 5/8 |
| Example 25 | 0.1 | 2 | 1:20 | 90 | 1a | 10 | 8/8 |
| Example 26 | 1 | 0.01 | 1:0.01 | 90 | 1a | 10 | 8/8 |
| Example 27 | 1 | 1 | 1:1 | 88 | 1a | 12 | 8/8 |
| Comparative Example 1 | 1 | — | 1:0 | 100 | — | — | 1/8 |
| Comparative Example 2 | 1 | 1 | 1:1 | 100 | — | — | 0/8 |
| Comparative Example 3 | 1 | — | 1:0 | 99.5 | 1a | 0.5 | 7/8 |
| Comparative Example 4 | — | 1 | 0:1 | 99.5 | 1a | 0.5 | 0/8 |
| Comparative Example 5 | 1 | 1 | 1:1 | 99.5 | 2 | 0.5 | 0/8 |

Referring to Table 1, with respect to the secondary batteries of Examples 1 to 27, since the first lithium salt increased the dissolution of metallic foreign matter and the compound represented by Formula 1 removed the dissolved metallic foreign matter by forming a complex with the metallic foreign matter, it may be understood that 60% or more of the prepared batteries were chargeable and dischargeable.

In contrast, with respect to the secondary battery of Comparative Example 1 which included the non-aqueous electrolyte solution not including the first lithium salt and the additive, it may be understood that the number of chargeable and dischargeable cells was 1.

Also, since the secondary battery of Comparative Example 2 including the non-aqueous electrolyte solution without an additive and the secondary battery of Comparative Example 5 including the compound of Formula 2, instead of the compound of Formula 1, as an additive, did not include an additive capable of adsorbing the metallic (Fe) foreign matter in which the dissolution thereof was increased by the first lithium salt, it may be understood that charge and discharge of all secondary batteries were not possible.

Furthermore, since the secondary battery of Comparative Example 4 including the non-aqueous electrolyte solution without the second lithium salt (LiPF$_6$) was severely corroded, charge and discharge of all secondary batteries were not possible.

With respect to the secondary battery of Comparative Example 3 including the non-aqueous electrolyte solution which did not include the first lithium salt, but only included the additive, it may be understood that most of the batteries were chargeable and dischargeable.

Experimental Example 2

Each of the secondary batteries prepared in Examples 1 to 25 and 27 and Comparative Examples 2, 4 and 5 was charged at a 0.8 C rate to 4.35 V under a constant current/constant voltage condition, cut-off charged at 0.05 C, and discharged at 0.5 C to a voltage of 3.0 V (initial discharge capacity). Subsequently, each of the secondary batteries was charged at a 0.8 C rate to 4.35 V under a constant current/constant voltage condition, cut-off charged at 0.05 C, and stored at 60° C. for 2 weeks. Thereafter, each battery was discharged at 0.5 C to a voltage of 3.0 V at room temperature and discharge capacity was measured (residual discharge capacity). Again, each battery was charged at a 0.8 C rate to 4.35 V under a constant current/constant voltage condition, cut-off charged at 0.05 C, and discharged at 0.5 C to a voltage of 3.0 V to measure discharge capacity (recovery discharge capacity). The residual discharge capacity and the recovery discharge capacity were expressed as a percentage (%) relative to the initial discharge capacity, and the results thereof are presented in the following Table 2.

Subsequently, discharging at 0.5 C to a voltage of 3.0 V at room temperature was set as one cycle, and capacity after 100 cycles was expressed as a percentage (%) relative to initial first cycle capacity and listed in Table 2 below.

In contrast, with respect to the secondary batteries of Comparative Examples 2 and 5, which respectively included the non-aqueous electrolyte solutions not including the compound of Formula 1 as an additive, and the secondary battery of Comparative Example 4 including the non-aqueous electrolyte solution without the second lithium salt, discharge capacity and capacity evaluation tests were not possible.

With respect to the secondary battery of Example 27 which included the non-aqueous electrolyte solution includ-

TABLE 2

| Examples | Lithium salt concentration (M) | | Molar ratio of second lithium salt:first lithium salt | Additive | | Residual discharge capacity (%) | Recovery discharge capacity (%) | Cycle capacity retention (%) |
|---|---|---|---|---|---|---|---|---|
| | Second lithium salt | First lithium salt | | Formula | Amount (g) | | | |
| Example 1 | 1 | 1 | 1:1 | 1a | 0.5 | 90 | 95 | 88 |
| Example 2 | 1 | 1 | 1:1 | 1b | 0.5 | 87 | 92 | 86 |
| Example 3 | 1 | 1 | 1:1 | 1c | 0.5 | 84 | 88 | 83 |
| Example 4 | 1 | 1 | 1:1 | 1d | 0.5 | 86 | 88 | 83 |
| Example 5 | 1 | 1 | 1:1 | 1e | 0.5 | 85 | 87 | 82 |
| Example 6 | 1 | 1 | 1:1 | 1f | 0.5 | 85 | 88 | 84 |
| Example 7 | 1 | 1 | 1:1 | 1g | 0.5 | 88 | 91 | 85 |
| Example 8 | 1 | 1 | 1:1 | 1h | 0.5 | 85 | 90 | 83 |
| Example 9 | 1 | 1 | 1:1 | 1i | 0.5 | 84 | 90 | 83 |
| Example 10 | 1 | 1 | 1:1 | 1j | 0.5 | 84 | 89 | 83 |
| Example 11 | 1 | 1 | 1:1 | 1k | 0.5 | 83 | 87 | 85 |
| Example 12 | 1 | 1 | 1:1 | 1l | 0.5 | 84 | 90 | 84 |
| Example 13 | 1 | 1 | 1:1 | 1m | 0.5 | 83 | 88 | 80 |
| Example 14 | 1 | 1 | 1:1 | 1n | 0.5 | 83 | 86 | 80 |
| Example 15 | 1 | 1 | 1:1 | 1o | 0.5 | 84 | 89 | 81 |
| Example 16 | 1 | 1 | 1:1 | 1a | 7 | 80 | 85 | 75 |
| Example 17 | 1 | 0.2 | 1:0.2 | 1a | 0.5 | 84 | 89 | 88 |
| Example 18 | 1 | 0.2 | 1:0.2 | 1b | 0.5 | 85 | 89 | 87 |
| Example 19 | 0.1 | 1 | 1:10 | 1a | 0.5 | 83 | 89 | 85 |
| Example 20 | 0.1 | 1 | 1:10 | 1b | 0.5 | 85 | 90 | 85 |
| Example 21 | 0.5 | 1 | 1:2 | 1a | 0.5 | 86 | 90 | 86 |
| Example 22 | 1 | 0.5 | 1:0.5 | 1a | 0.5 | 84 | 90 | 90 |
| Example 23 | 1 | 1 | 1:1 | 1a | 10 | 78 | 80 | 72 |
| Example 24 | 0.1 | 2 | 1:20 | 1a | 0.1 | 87 | 90 | 80 |
| Example 25 | 0.1 | 2 | 1:20 | 1a | 10 | 86 | 87 | 74 |
| Example 27 | 1 | 1 | 1:1 | 1a | 12 | 78 | 80 | 68 |
| Comparative Example 2 | 1 | 1 | 1:1 | — | — | — | — | — |
| Comparative Example 4 | — | 1 | 0:1 | 1a | 0.5 | — | — | — |
| Comparative Example 5 | 1 | 1 | 1:1 | 2 | 0.5 | — | — | — |

Referring to Table 2, with respect to the secondary batteries of Examples 1 to 25 which respectively included the non-aqueous electrolyte solutions including all of the first lithium salt, the second lithium salt, and the compound of Formula 1, residual discharge capacities during high-temperature storage were about 78% or more, recovery discharge capacities were about 80% or more, and cycle capacity retentions were about 72% or more, wherein it may be understood that the residual capacities, recovery capacities, and cycle capacity retentions were all excellent. Particularly, the cycle capacity retentions of the secondary batteries of Examples 1 to 12, which respectively included the non-aqueous electrolyte solutions respectively including the compounds of Formulae 1a to 1l as an additive, were better than those of the secondary batteries of Examples 13 to 15 which respectively included the non-aqueous electrolyte solutions respectively including the compounds of Formulae 1m to 1o as an additive.

ing all of the first lithium salt, the second lithium salt, and the compound of Formula 1, residual discharge capacity, recovery discharge capacity, and cycle capacity retention were all better than those of the secondary batteries of Comparative Examples 2, 4, and 5, but it may be understood that the cycle capacity retention was relatively reduced in comparison to those of the secondary batteries of Examples 1 to 25 due to the increase in resistance caused by the excessive amount of the additive used.

Experimental Example 3

After each of the secondary batteries prepared in Examples 1 to 27 and Comparative Examples 1 to 3 was charged at a 0.8 C rate to 4.2 V under a constant current/constant voltage condition and stored at 45° C. for 6 days, voltages at 45° C. were measured and an average value thereof is listed in the following Table 3.

Also, after 6 days of storage, the secondary batteries prepared in Examples 1, and 24 to 27 and Comparative Example 3 were further stored at 45° C. for 9 days (total storage time 15 days), voltages at 45° C. were then measured, and the lowest voltage is listed in the following Table 3.

TABLE 3

| Examples | Lithium salt concentration (M) | | Molar ratio of second lithium salt:first lithium salt | Additive | | Voltage after high-temperature storage (V) | |
|---|---|---|---|---|---|---|---|
| | Second lithium salt | First lithium salt | | Formula | Amount (g) | 6 days/ average | 15 days/ lowest |
| Example 1 | 1 | 1 | 1:1 | 1a | 0.5 | 4.15 | 4.05 |
| Example 2 | 1 | 1 | 1:1 | 1b | 0.5 | 4.07 | — |
| Example 3 | 1 | 1 | 1:1 | 1c | 0.5 | 4.02 | — |
| Example 4 | 1 | 1 | 1:1 | 1d | 0.5 | 4.05 | — |
| Example 5 | 1 | 1 | 1:1 | 1e | 0.5 | 4.08 | — |
| Example 6 | 1 | 1 | 1:1 | 1f | 0.5 | 4.09 | — |
| Example 7 | 1 | 1 | 1:1 | 1g | 0.5 | 4.13 | — |
| Example 8 | 1 | 1 | 1:1 | 1h | 0.5 | 4.06 | — |
| Example 9 | 1 | 1 | 1:1 | 1i | 0.5 | 4.04 | — |
| Example 10 | 1 | 1 | 1:1 | 1j | 0.5 | 4.06 | — |
| Example 11 | 1 | 1 | 1:1 | 1k | 0.5 | 4.02 | — |
| Example 12 | 1 | 1 | 1:1 | 1l | 0.5 | 4.03 | — |
| Example 13 | 1 | 1 | 1:1 | 1m | 0.5 | 4.04 | — |
| Example 14 | 1 | 1 | 1:1 | 1n | 0.5 | 4.01 | — |
| Example 15 | 1 | 1 | 1:1 | 1o | 0.5 | 4.01 | — |
| Example 16 | 1 | 1 | 1:1 | 1a | 7 | 4.00 | — |
| Example 17 | 1 | 0.2 | 1:0.2 | 1a | 0.5 | 4.07 | — |
| Example 18 | 1 | 0.2 | 1:0.2 | 1b | 0.5 | 4.08 | — |
| Example 19 | 0.1 | 1 | 1:10 | 1a | 0.5 | 4.05 | — |
| Example 20 | 0.1 | 1 | 1:10 | 1b | 0.5 | 4.00 | — |
| Example 21 | 0.5 | 1 | 1:2 | 1a | 0.5 | 4.08 | — |
| Example 22 | 1 | 0.5 | 1:0.5 | 1a | 0.5 | 4.05 | — |
| Example 23 | 1 | 1 | 1:1 | 1a | 10 | 3.90 | — |
| Example 24 | 0.1 | 2 | 1:20 | 1a | 0.1 | 3.73 | 3.66 |
| Example 25 | 0.1 | 2 | 1:20 | 1a | 10 | 3.88 | 3.90 |
| Example 26 | 1 | 0.01 | 1:0.01 | 1a | 10 | 3.81 | 3.72 |
| Example 27 | 1 | 1 | 1:1 | 1a | 12 | 3.85 | 3.80 |
| Comparative Example 1 | 1 | — | 1:0 | — | — | 2.08 | — |
| Comparative Example 3 | 1 | — | 1:0 | 1a | 0.5 | 4.00 | 3.55 |

Referring to Table 3, it may be understood that the secondary batteries of Examples 1 to 27 maintained a voltage of about 3.73 V or more even after 6 days of storage at a high temperature. Particularly, it may be understood that the secondary batteries of Examples 24 to 27 maintained a voltage of about 3.66 V or more even after 15 days of storage at a high temperature. In this case, with respect to the secondary battery of Example 27 in which the amount of the compound of Formula 1a having a high effect of adsorbing the metallic foreign matter was large, it may be understood that it exhibited a lower voltage drop than the secondary battery of Example 24.

In contrast, with respect to the secondary battery of Comparative Example 1 including the non-aqueous electrolyte solution which did not include the first lithium salt and the compound of Formula 1, it may be understood that the voltage was significantly reduced to 2.08 V after 6 days of storage at a high temperature.

Also, with respect to the secondary battery of Comparative Example 3 which did not include the first lithium salt, but only included the additive, it maintained a voltage of 4.00 V after 6 days of storage, but, since the dissolution of the metallic foreign matter was not initially completed but continuously occurred, the voltage was significantly reduced to 3.55 V after 15 days of storage, and thus, it may be understood that the abnormal voltage drop phenomenon occurred.

The invention claimed is:

1. A non-aqueous electrolyte solution for a lithium secondary battery, consisting of:

a first lithium salt that is lithium bis(fluorosulfonyl)imide (LiFSI);

a second lithium salt excluding the LiFSI;

an organic solvent selected from an ether-based solvent, an ester-based solvent, an amide-based solvent or as a mixture thereof, wherein the ester-based solvent is at least one selected from the group consisting of a cyclic carbonate compound, a linear carbonate compound, an alkyl ether-based compound, an alkyl acetate-based compound, and an alkyl propionate-based compound, and the cyclic carbonate compound is at least one selected from the group consisting of ethylene carbonate (EC), propylene carbonate (PC), 1,2-butylene carbonate, 2,3-butylene carbonate, 1,2-pentylene carbonate, 2,3-pentylene carbonate, and fluoroethylene carbonate (FEC);

a compound represented by Formula 1; and optionally, an additive selected from the group consisting of a sultone-based compound, a halogen-substituted carbonate-based compound, a nitrile-based compound, a cyclic sulfite-based compound, and a cyclic carbonate-based compound that is vinyl ethylene carbonate, wherein the sultone-based compound is at least one of 1,3-propane sultone (PS), 1,4-butane sultone, ethene sultone, 1,4-butene, sultone, or 1-methyl-1,3-propene sultone, wherein a molar ratio of the second lithium salt to the first lithium salt is in a range of 1:1 to 1:2, and wherein the compound represented by Formula 1 is included in an amount of 0.1 wt % to 7 wt % based on a total amount of the non-aqueous electrolyte solution:

(Formula 1)

wherein, in Formula 1, $R_1$ to $R_3$ are each independently hydrogen or an alkyl group having 1 to 6 carbon atoms, and A is wherein, $R_5$ is hydrogen, an aryl group having 6 to 8 carbon atoms that is unsubstituted or substituted with at least one fluorine atom, or an alkynyl group having 2 to 6 carbon atoms.

2. The non-aqueous electrolyte solution for a lithium secondary battery of claim 1, wherein the first lithium salt is included in a concentration of 0.01 M to 3 M in the non-aqueous electrolyte solution.

3. The non-aqueous electrolyte solution for a lithium secondary battery of claim 1, wherein $R_5$ is hydrogen, an unsubstituted aryl group having 6 to 8 carbon atoms, a phenyl group substituted with an alkyl group having 1 to 3 carbon atoms, a phenyl group substituted with at least one fluorine atom, or an alkynyl group having 2 to 6 carbon atoms.

4. The non-aqueous electrolyte solution for a lithium secondary battery of claim 1, wherein the compound represented by Formula 1 comprises at least one a compound represented by Formulae 1l:

(Formula 1l)

5. The non-aqueous electrolyte solution for a lithium secondary battery of claim 1, wherein the compound represented by Formula 1 is included in an amount of 0.5 wt % to 7 wt % based on a total amount of the non-aqueous electrolyte solution.

6. A lithium secondary battery comprising the non-aqueous electrolyte solution of claim 1.

7. A non-aqueous electrolyte solution for a lithium secondary battery, consisting of:

a first lithium salt that is lithium bis(fluorosulfonyl)imide (LiFSI);

a second lithium salt that is $LiPF_6$;

an organic solvent selected from an ether-based solvent, an ester-based solvent, an amide-based solvent or as a mixture thereof, wherein the ester-based solvent is at least one selected from the group consisting of a cyclic carbonate compound, a linear carbonate compound, an alkyl ether-based compound, an alkyl acetate-based compound, and an alkyl propionate-based compound, and the cyclic carbonate compound is at least one selected from the group consisting of ethylene carbonate (EC), propylene carbonate (PC), 1,2-butylene carbonate, 2,3-butylene carbonate, 1,2-pentylene carbonate, 2,3-pentylene carbonate, and fluoroethylene carbonate (FEC);

a compound represented by Formula 1; and optionally, an additive selected from the group consisting of a sultone-based compound, a halogen-substituted carbonate-based compound, a nitrile-based compound, a cyclic sulfite-based compound, and a cyclic carbonate-based compound that is vinyl ethylene carbonate, wherein the sultone-based compound is at least one of 1,3-propane sultone, (PS), 1,4-butane sultone, ethene sultone, 1,4-butene sultone, or 1-methyl-1,3-propene sultone, wherein a molar ratio of the second lithium salt to the first lithium salt is in a range of 1:1 to 1:2, and wherein the compound represented by Formula 1 is included in an amount of 0.1 wt % to 7 wt % based on a total amount of the non-aqueous electrolyte solution:

(Formula 1)

wherein, in Formula 1, $R_1$ to $R_3$ are each independently hydrogen or an alkyl group having 1 to 6 carbon atoms, and A is wherein, $R_4$ is hydrogen, an alkyl group having 1 to 6 carbon atoms that is unsubstituted or substituted with at least one fluorine atom, an aryl group having 6 to 8 carbon atoms that is unsubstituted or substituted with at least one fluorine atom, or an alkynyl group having 2 to 6 carbon atoms, and

$R_5$ is hydrogen, an aryl group having 6 to 8 carbon atoms that is unsubstituted or substituted with at least one fluorine atom, or an alkynyl group having 2 to 6 carbon atoms.

8. The non-aqueous electrolyte solution for a lithium secondary battery of claim 7, wherein the first lithium salt is included in a concentration of 0.01 M to 3 M in the non-aqueous electrolyte solution.

9. The non-aqueous electrolyte solution for a lithium secondary battery of claim 7, wherein $R_4$ is hydrogen, an alkyl group having 1 to 6 carbon atoms that is unsubstituted or substituted with at least one fluorine atom, an unsubstituted aryl group having 6 to 8 carbon atoms, a phenyl group substituted with an alkyl group having 1 to 3 carbon atoms, a phenyl group substituted with at least one fluorine atom, or an alkynyl group having 2 to 6 carbon atoms, and $R_5$ is hydrogen, an unsubstituted aryl group having 6 to 8 carbon atoms, a phenyl group substituted with an alkyl group having 1 to 3 carbon atoms, a phenyl group substituted with at least one fluorine atom, or an alkynyl group having 2 to 6 carbon atoms.

10. The non-aqueous electrolyte solution for a lithium secondary battery of claim 7, wherein the compound represented by Formula 1 comprises at least one compound represented by Formulae 1a to 1g, or 1l:

(Formula 1a)

(Formula 1b)

(Formula 1c)

(Formula 1d)

(Formula 1e)

(Formula 1f)

(Formula 1g)

(Formula 1l)

11. The non-aqueous electrolyte solution for a lithium secondary battery of claim 7, wherein the compound represented by Formula 1 is included in an amount of 0.5 wt % to 7 wt % based on a total amount of the non-aqueous electrolyte solution.

12. A lithium secondary battery comprising the non-aqueous electrolyte solution of claim 7.

* * * * *